United States Patent [19]
Cantello et al.

[11] 4,017,639
[45] Apr. 12, 1977

[54] 2-HYDROXY-3-NITRO-1,4-NAPHTHOQUINONES FOR THE PROPHYLAXIS OF CERTAIN ALLERGIES

[75] Inventors: Barry Christian Charles Cantello, Horsham; Derek Richard Buckle, Redhill; Harry Smith, Maplehurst, near Horsham, all of England

[73] Assignee: Beecham Group Limited, Great Britain

[22] Filed: Mar. 12, 1976

[21] Appl. No.: 666,260

Related U.S. Application Data

[62] Division of Ser. No. 571,253, April 24, 1975.

[30] Foreign Application Priority Data

May 28, 1974  United Kingdom ............. 23563/74

[52] U.S. Cl. .............................................. 424/331
[51] Int. Cl.² ........................................ A61K 31/12
[58] Field of Search ................................... 424/331

[56] References Cited

UNITED STATES PATENTS 3,833,726  9/1974  Schwender et al. ........... 424/331 X
3,920,845  11/1975  Smith et al. ...................... 424/331

OTHER PUBLICATIONS

Vladimirtsev et al., Chemical Abstracts 73:1190f, (1970).
Ikeda et al., Chemical Abstracts 50:3358d, (1956).

*Primary Examiner*—Norman A. Drezin

[57] ABSTRACT

Substituted naphthoquinones of the formula (I) and pharmaceutically acceptable salts thereof wherein $R_1$, $R_2$, $R_3$ and $R_4$ represent alkyl, aryl, alkoxy, hydroxy, hydrogen or halogen or any two of the groups $R_1$, $R_2$, $R_3$ and $R_4$ taken together complete a carbocyclic ring, have useful anti-allergy activity in mammals.

34 Claims, No Drawings

2-HYDROXY-3-NITRO-1,4-NAPHTHOQUINONES FOR THE PROPHYLAXIS OF CERTAIN ALLERGIES

CROSS-REFERENCE

This is a division of Ser. No. 571,253 filed Apr. 24, 1975.

This invention relates to pharmaceutical compositions which are useful in the inhibition of the effects of certain types of antigen-antibody reactions, and are therefore of the value in the prophylaxis and treatment of diseases associated with allergic or immunological reaction e.g. certain types of asthma and hay-fever and also in the treatment of rhinitis. The invention also includes a number of new substituted nitro-tri-keto tetralins and a method for their preparation, as well as intermediates useful in their preparation.

2-Hydroxy-3-nitro-1,4-naphthoquinones of formula (I):

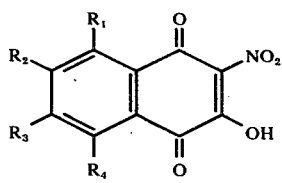

and pharmaceutically acceptable salts thereof, wherein the groups $R_1$, $R_2$, $R_3$ and $R_4$ are each a hydrogen or halogen atom, or an alkyl, aryl, alkoxy or hydroxy and any two of the groups $R_1$, $R_2$, $R_3$ and $R_4$ taken together may complete a carbocyclic ring, have useful activity in mammals in that they inhibit the effects of certain types of antigen-antibody reactions.

A literature search has revealed that one of the compounds of the formula (I) is not novel. More specifically, the compound 2-hydroxy-3-nitro-1,4-naphthoquinone has been reported by K. Miyaka and N. Ikeda, J. Pharm Soc. Japan. 74, 655, 1954. However no form of useful biological activity has been ascribed to the compound. Likewise there has been in the literature, no suggestion that such a acompound is likely to possess any form of useful biological activity and in particular the discovery that it has anti-allergic activity has not been predicted in any way.

Accordingly, in its broadest aspect, the present invention provides a pharmaceutical composition having anti-allergy activity comprising a compound of formula (I) or a pharmaceutically acceptable salt thereof:

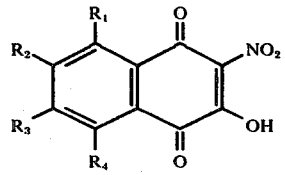

together with one or more pharmaceutically acceptable carriers, wherein the groups $R_1$, $R_2$, $R_3$ and $R_4$ represent hydrogen, alkyl, alkoxy, aryl, hydroxy or halogen and any two of the groups $R_1$, $R_2$, $R_3$ and $R_4$ taken together complete a carbocyclic ring being adapted for administration to human beings.

Examples of the groups $R_1$, $R_2$, $R_3$ and $R_4$ which may be present in compounds of the formula (I) include hydrogen, fluorine, chlorine, bromine and iodine atoms, and methyl, ethyl, n- and iso- propyl, n-, sec- and tert-butoxy, phenyl. In addition the groups $R_2$ and $R_2$, $R_2$ and $R_3$ or $R_3$ and $R_4$ taken together may complete benzene, cyclohexenyl or cyclopentenyl ring.

Preferably the groups $R_1$ and $R_4$ are each hydrogen atoms, and the groups $R_2$ and $R_3$ are each methyl, ethyl, n-proply, methoxy, ethoxy or n-propoxy groups, or $R_2$ and $R_3$ taken together complete cyclohexenyl or cyclopentenyl ring.

Examples of suitable salts of compounds of the formula (I) include the alkali metal salts, particularly potassium and sodium, and the alkaline earth metal salts, magnesium salts or aluminium salts, as well as salts with organic bases such as amines or amino compounds.

The compounds of formula (I) may exist in a number of tautomeric forms, and it is to be understood that whenever in the specification we refer to compounds of the formula (I) we mean to include tautomeric forms thereof.

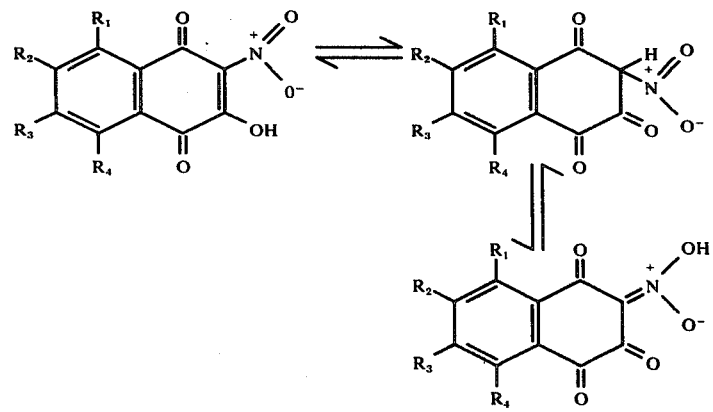

The compositions of this invention may be presented as a microfine powder for insufflation, e.g. as a snuff or in capsules of hard gelatin. They may also be presented with a sterile liquid carrier for injection. Compounds of formula (I) which are active when given by the oral route, may be compounded in the form of syrups, tablets, capsules, pills and the like. Preferably the compositions are in unit dosage form, or in a form which the patient can administer to himself in a single dosage. For example when the composition is in the form of a tablet, pill or capusle, a suitable dosage unit might contain from 1 to 500 mg of active ingredient. If desired, a small amount of bronchodilator compound such as isoprenaline may be incorporated into the compositions of this invention both to inhibit the cough response if the composition is insufflated and to provide immediate relief during an asthmatic attack. The effective dose of compound (I) depends on the particular compound employed, but is in general in the range of from 0.1 mg/kg/day to 100 mg/kg/day.

The precise nature of the pharmaceutical carrier used in the compositions of this invention is not important. Standard pharmaceutical practice may be followed.

As is common practice, the compositions will usually be accompanied by written or printed directions for use in the medical treatment concerned, in this case as an anti-allergic agent for prophylaxis treatment of, for example, asthma, hay-fever or rhinitis.

In a second aspect, the invention provides novel compounds of the formula (I):

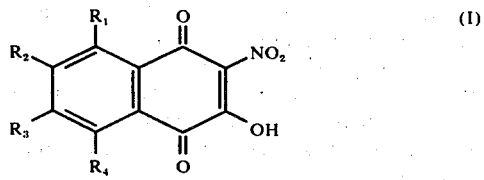

and pharmaceutically acceptable salts thereof, wherein the groups $R_1$, $R_2$, $R_3$ and $R_4$ are each a hydrogen or halogen atoms, or an akyl, aryl, aralkyl, alkoxy, aryloxy aralkoxy, heterocyclic, or hydroxy, and any two of the groups $R_1$, $R_2$, $R_3$ and $R_4$ taken together may complete a carbocyclic ring; except the compound 2-hydroxy-3-nitro-1,4-naphthoquinone and pharmaceutically acceptable salts thereof.

The identities and the preferred values of the groups $R_1$, $R_2$, $R_3$ and $R_4$ have already been discussed in relation to the pharmaceutical compositions of the invention, and the same remarks apply here in relation to these novel compounds.

The invention further provides a process for the preparation of these novel compounds, which process comprises nitrating the parent compound of the formula (II):

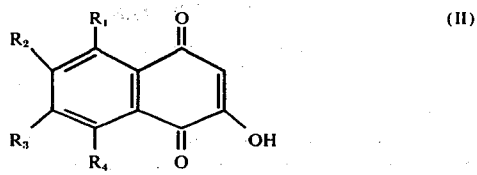

wherein the groups $R_1$, $R_2$, $R_3$ and $R_4$ are as defined with reference to formula (I), except that compound in which the groups $R_1$, $R_2$, $R_3$ and $R_4$ are not all hydrogen atoms, and thereafter if desired converting the thus formed compound of the formula (I) to a pharmaceutically acceptable salt thereof.

As nitrating agent we prefer to use fuming nitric acid, and the reaction is suitably carried out in an inert solvent at an ambient or slightly lowered temperature. While the choice of solvent and temperature is not critical to the success of the reaction, we have found that the reaction procedes smoothly in chloroform at room temperature.

Other conventional nitrating agents may be used to effect the required conversion. These include:

i. The nitrous fumes generated with concentrated nitric acid and arsenic oxide.

ii. Acetic acid together with concentrated nitric acid.

iii. Concentrated nitric acid.

The 2-hydroxy-1,4-naphthoquine precursors used in the preparation of the novel compounds of this invention may be prepared by two routes. The method of choice will depend upon the nature of the substitution required, and the availability of starting materials.

Route 1 involves the Diels-Alder addition of a suitable 1,3-diene (III) to p-benzoquinone. The resultant Diels-Alder adduct (IV) is isomerised and oxidised to a 1,4-naphthoquinone (V):

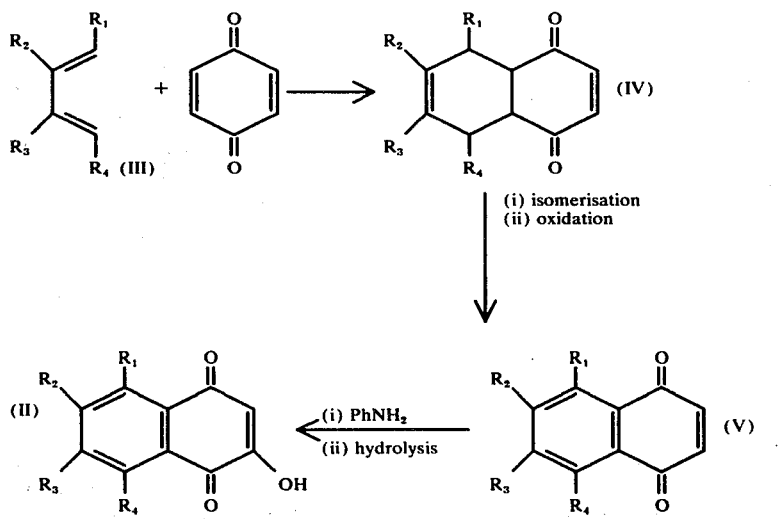

The 1,4-naphthoquinone is reacted with aniline, according to the method of Lyons & Thomson, J. Chem. Soc. 1953 Page 910, and the product then hydrolysed with, for example, dilute sulphuric acid, to yield the corresponding compound of the formula (II). (When the groups $R_1$, $R_2$, $R_3$ and $R_4$ are such that the compound of the formula (V) is asymmetrically substituted in the phenyl ring, the position of hydroxyl substitution to be expected in the quinone ring is discussed by Lyons and Thomson, loc. cit., and Macleod and Thomson, J. Org. Chem. 25, 36, (1960)).

Route 2 involves the Friedel-Craft acylation of a substituted benzene (VI) with succinic anhydride, to yield a keto acid (VIII). This keto acid is reduced and cyclized with polyphosphoric acid to yield the tetralone (VIII). Tetralones of formula (VIII) can be readily converted to 2-hydroxy-1,4-naphthoquinones of formula (IX) by autoxidation using the procedures disclosed by Baillie and Thomson in J. Chem. Soc. (C) 1966, page 2184 and by Kasturi and Arunachalam in Canad. J. Chem. 1966 vol. 44 page 1086.

(1960). (Found; C, 54.99; H, 2.59; N, 6.30; $C_{10}H_5NO_5$ requires; C 54.80; H, 2.30; N, 6.39%).

b. A suspension of 2,3-dichloro-1,4naphthoquinone (6,83g; 0.03 mole) in methanol (40ml) was stirred during the addition of a solution of sodium nitrate (6.9g; 0.1 mole) in water (50ml) and the mixture stirred at 80° C for 3 hrs. Solution was attained after about 1 hr and the nitro naphthoquinone began to separate after 2 hrs. After cooling in ice and the yellow crystalline solid was filtered off, taken up in water (200ml), charcoalised and precipitated the product by addition of one-third the volume of concentrated hydrochloric acid, filtered off, washed well with 5N HCl and dried in vacuo over $P_2O_5$/NaOH to give 5.30 g

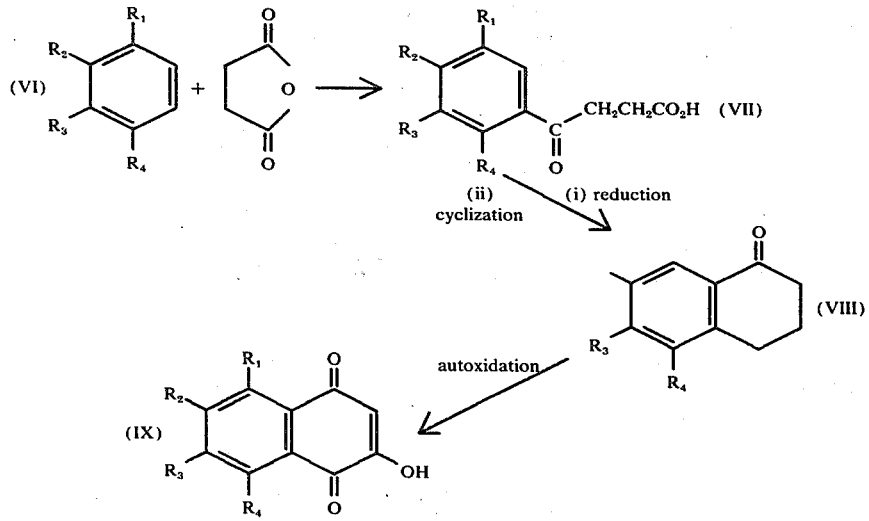

The novel compounds of formula (I) can also be prepared from the intermediates of formula (X):

wherein $R_1$, $R_2$, $R_3$ and $R_4$ are defined as in formula (I), which process comprises reacting the intermediates with sodium nitrite in aqueous alkanol. (Miyaka & Ikeda Loc. Cit.)

The novel intermediates of formula (X) are prepared from substituted 1,4-naphthoquinone of formula (V) by direct chlorination using standard procedures.

EXAMPLE 1

2-Hydroxy-3-nitro-1,4naphthoquinone a. Fuming nitric acid (10ml; d 1.52) was added to a stirred suspension of 2-hydroxy-1,4-naphthoquinone (2.0g) in chloroform (200ml) at room temperature over 1 hr. After a further 1 hr. the solvent was removed in vacuo without heating and 5N hydrochloric acid (50ml) was added to the residue. Filtration gave 1,84g (73%) of yellow product of m.p. 152°–153° C (d). Recrystallisation from water; hydrochloric acid gave material of m.p. 161–2° C (d). (Lit m.p. 160°–161° C A. Inoue, N. Kuroki and K. Konishi CA 54 4504 g (81%) of material of m.p. 162°–163° C (d) which was identical to that prepared above.

EXAMPLE 2

2-Hydroxy-6-methyl-3-nitro-1,4-naphthoquinone

Fuming nitric acid (5ml, d 1.52) was added to a stirred suspension of 2-hydroxy-6-methyl-1,4-naphthoquinone (1.0g) in chloroform (100ml) over 1 hr. at room temperature and after a further 1 hr. the yelllow product, 0.09g (73%) was isolated as in example 1(a). Recrystallisation from water; hydrochloric acid gave m.p. 159°–160° C (d). (Found; C, 56.57; H, 3.04; N, 5.88; $C_{11}H_7NO_5$ requires; C, 56.66; H, 3.03; N, 6.01%).

EXAMPLE 3

3,5-Dihydroxy-2-nitro-1,4-naphthoquinone

Nitration of 3,5-dihydroxy-1,4-naphthoquinone (1.04g) as described in example 1(a) afforded 0.654g (51%) of the 2-nitro derivative as orange needles. Recrystallisation from water; hydrochloric acid gave m.p. 168°–169° C (d). )Found; C, 50.31; H, 2.09; N, 6.04; $C_{10}H_5NO_6$ requires; C, 51.08; H, 2.14; N, 5.96%).

EXAMPLE 4

3-Hydroxy-5-methyl-2-nitro-1,4-naphthoquinone

A solution of 3-hydroxy-5-methyl-1,4-naphthoquinone (1.9g) in chloroform (200ml) was nitrated with fuming nitric acid according to example 1(a). A yield of 1.01g (43%) of material of m.p. 148°–149° C (d) was obtained. (Found; C, 56.69; H, 3.16; N, 5,73; $C_{11}H_7NO_5$ requires; C, 56.66; H, 3.03; N, 6.01%).

EXAMPLE 5

3-Hydroxy-6-methoxy-2-nitro-1,4-naphthoquinone

Nitration of a stirred solution of 3-hydroxy-6-methoxy-1,4-naphthoquinone (2g) as described in example 1(a) gave 2.29g (94%) of the nitro derivative of m.p. 152°–155° C. Recyrstallisation from water; hydrochloric acid raised the m.p. to 159° C. (Found; C, 53.11; H, 3.03; N, 5.78; $C_{11}H_7NO_6$ requires; C, 53.01; H, 2.83; N, 5.62%).

EXAMPLE 6

3-Hydroxy-6-methyl-2-nitro-1,4-naphthoquinone

Nitration of 3-hydroxy-6-methyl-1,4-naphthoquinone (2.0g) as described in example 1(a) gave 2.41g (97%) of the yellow 2-nitro derivative of m.p. 160° C. (Found; C, 56.73; H, 3.00; N, 5.75; $C_{11}H_7NO_5$ requires; C, 56.66; H, 3.03; N, 6.01%).

EXAMPLE 7 a. 2-Anilino-6,7-dimethyl-1,4-naphthoquinone

To a warm solution of 6,7-dimethyl-1,4-naphthoquinone (1.08g; 0.058 mole) in ethanol (20ml) was added aniline (0.5ml) and the red solution refluxed for 1 hr. on a steam bath. After standing overnight the red crystalline anilino derivative was filtered off and recrystallised from acetic acid; water to give 0.54g (34%) of material of m.p. 208°–210° C. (Found C, 78.02; H, 5,47; N, 4.88; $C_{18}H_{15}NO_2$ requires; C, 77.96; H, 5.45; N, 5.05%).

b. 6,7-Dimethyl-2-hydroxy-1,4-naphthoquinone

A solution of 2-anilino-6,7-dimethyl-1,4naphthoquinone (3.1; 0.014 mole) in concentrated sulphuric acid (70ml) was diluted with an equal volume of water and refluxed for 1 minute. After pouring into cold water the precipitated hydroxy derivative was filtered off and extracted into petrol ether (b.p. 100°–102° C). After treatment of the extract with charcoal the title compound separated as a yellow solid, 1.29g (55%), m.p. 175°–177° C (d). (Found; C, 71.29; H, 5.07 $C_{12}H_{10}O_3$ requires; C, 71.28; H, 4.98%)

c. 6,7-Dimethyl-2-hydroxy-3-nitro-1,4-naphthoquinone

Nitration of 6,7-dimethyl-2-hydroxy-1,4-naphthoquinone (1.0g; 0.0056 mole) in chloroform (100ml) as described in example 1(a) afforded 1.027g (87%) of material of m.p. 166°–169° C (d). Recrystallisation from ethanol; hydrochloric acid raised the m.p. to 169°–170°C (d). (Found; C, 58.15; H, 3.76; N, 5.74; $C_{12}H_9NO_5$ requires; C, 58.30; H, 3.67; N, 5.6%)

EXAMPLE 8 a. 7-Ethoxyl-1-tetralone

A mixture of 4-(p-ethoxyphenyl) butanoic acid (77g, m.p. 136°–138° C, prepared by the Clemmensen reduction of 3-(p-ethoxybenzoyl) propanoic acid) and 85% polyphosphoric acid (500g) was heated with stirring at 80° C for 30 mins. The resulting solution was cooled and poured onto 2Kg of ice-water and the precipitated tetralone extracted into ether. The organic phase was washed with water, saturated sodium bicarbonate solution and water, dried (Mg $SO_4$), and the solvent removed. Distillation of the residue afforded the tetralone $bp_{0.1}$ 164°–168° C., 41.62g (60%) as a white solid. Recrystallisation from 40°–60° C petrol gave material of m.p. 34°–36° C. (Found; C, 75.65; H, 7.29; $C_{12}H_{14}O_2$ requires; c, 75.76; H, 7.46%)

b. 6-Ethoxy-3-hydroxy-1,4-naphthoquinone

7-Ethoxy-1tetralone (37g; 0.195 mole) was added to 1 molar solution of potassium t-butoxide in dry t-butanol (1600ml) previously saturated with oxygen and the mixture stirred under an oxygen atmosphere until 0.39 mole of oxygen (2 equivs) were absorbed (ca. 15–30 mins.). The resulting solution was cooled (exothermic reaction), acidified with concentrated hydrochloric acid and the t-butanol removed in vacuo. The residue was partitioned between water and chloroform and the organic phase separated. Extraction of the hydroxy quinone with sodium bicrbonate followed by re-acidification afforded, after filtration and drying 19.75g (46%) of material of m.p. 185+ C (d). Recrystallisation from ethanol in the presence of charcoal increased the m.p. to 188° C (d). (Found; C, 66.13; H, 4.85; $C_{12}H_{10}O_4$ requires; C, 66.05; H, 4.62%)

c. 6-Ethoxy-3-hydroxy-2-nitro-1,4-naphthoquinone

Nitration of 6-ethoxy-3-hydroxy-1,4-naphthoquinone (2g; 0.092 mole) according to example 1(a) yielded 2.38g (99%) of the 2-nitro derivative. Recrystallisation from water; hydrochloric acid gave material of m.p. 158+ C (d). (Found; C, 54.89; H, 3.61; N, 5.14; $C_{12}H_9NO_6$ requires; C, 54.75; H, 3.45; N, 5.32%).

EXAMPLE 9

6.7-Dimethoxy-2-hydroxy-3-nitro-1,4-naphthoquinone

A solution of 6,7-dimethoxy-2-hydroxy-1,4-naphthoquinone (2g) in chloroform (200ml) was nitrated with fuming nitric acid at room temperature. Work-up as described in example 1(a) gave 1.88g (79%) of nitro derivative of m.p. 178°–181° C. Recrystallisation from water; hydrochloric acid gave m.p. 181°–184° C. (Found; C, 51.72; H, 3.30; N, 5.08; $C_{12}H_9NO_7$ requires; C, 51.62; H, 3.25; N, 5.02%).

EXAMPLE 10 a. 6-Bromo-3-hydroxy-1,4- naphthoquinone

Autoxidation of 7-bromo-1-tetralone (4g; 0.0178 mole) as described in example 8(b) afforded 1.52g (34%) of the title compound of m.p. 197° C. Recrystallisation from ethanol raised the m.p. to 216° C. (Found; C, 47.50; H, 2.12; Br, 31.43; $C_{10}H_5BrO_3$ requires; C, 47.49; H, 1.99; Br, 31.60%).

b. 6-Bromo-3-hydroxy-2-nitro-1.4-naphthoquinone

Nitration of 6-bromo-3-hydroxy-1,4-naphthoquinone (0.82g) in chloroform (100ml) as described in example 1(a) gave 0.80g (81%) of the nitro derivative, m.p. 172° C. (Found; C, 40.30; H, 1.43; N, 4.55; Br, 26.80; $C_{10}H_4BrNO_5$ requires; C, 40.29; H, 1.35; N, 4.70; Br, 26.81%).

EXAMPLE 11 a. 7-Fluoro-1-tetralone

A stirred mixture of 4-(p-fluorophenyl) butanoic acid (23g; 0.126 mole) and 85% polyphosphoric acid (200g) was heated at 100° C for 4 hrs., cooled, and poured onto ice-water (800g). After through stirring the precipitated tetralone was filtered off, washed well with water, and recrystallised from ethanol to give 13.07g (63%) of material of m.p. 56°–57° C. (Found; C, 73.31; H, 5.72; $C_{10}H_9FO$ requires; C, 73.13; H, 5,53%).

b. 6-Fluoro-3-hydroxy-1,4-naphthoquinone

Autoxidation of 7-fluoro-1-tetralone (13g) as described in example 8(b) gave 5.6g (37%) of the naphthoquinone which after recrystallisation from chloroform had m.p. 206°–210° C. (Found; C, 62.50; H, 2.70; $C_{10}H_5FO_3$ requires; C, 62.51; H, 2.62%).

c. 6-Fluoro-3-hydroxy-2-nitro-1,4-naphthoquinone

Nitration of 6-fluoro-3-hydroxy-1,4-naphthoquinone (1.0g) as described in example 1(a) afforded 0.81g (66%) of product of m.p. 152° C. (Found; C, 50.28; H, 1.61; H, 5.61; $C_{10}H_4FNO_5$ requires; C, 50.65; H, 1.70; N, 5.91%).

EXAMPLE 12 a. 6,7-Diethyl-1-tetralone 3-(3',4'-Diethylenzoyl) propanoic acid (m.p. 93° C, prepared by the acylation of 1,2-diethyl benzene with succinic anhydride) was catalytically reduced to 4-(3',-4'-diethylphenyl) butanoic acid (b.p.$_{0.7}$ 143°–147° C). A mixture of this acid (59g; 0.27 mole) and 85% polyphosphoric acid (450g) was warmed to 80° C with stirring for 30 mins. and worked up as in example 8(a) to yield 48.30g (89%) of 6,7-diethyl-1-tetralone, b.p.$_{0.7}$ 118°–122° C. (Found; C, 82.95; H, 9.21; $C_{14}H_{18}O$ requires; C, 83.12; H, 8.97%). Alternatively 4-(3', 4'-diethylphenyl )butanoic acid (23.3g; 0.106 mole) may be cyclised by stirring at 100° C with 80% sulphuric acid (115ml) for 1½ hrs. After dilution, extraction into ether and distillation 15.53g (74%) of the tetralone was recovered.

b. 6,7-Diethyl-2-hydroxy-1,4-naphthoquinone

Autoxidation of 6,7-diethyl-1-tetralone (48g; 0.24 mole ) with potassium t-butoxide in t-butanol as described in example 8(b) afforded 34.60g (63%) of the title compound. Recrystallisation from aqueous ethanol in the presence of charcoal gave a yellow crystalline solid of m.p. 105°–109° C. (Found; C, 70.45; H, 6.10; $C_{14}H_{14}O_3·½H_2O$ requires; C, 70.28; H, 6.32%).

c. 6,7-Diethyl-2-hydroxy-3-nitro-1,4-naphthoquinone

Nitration of 6,7-diethyl-2-hydroxy-1,4-naphthoquinone (2.0g) as described in example 1(a) gave 1.794g (75%) of material of m.p. (EtOH; $H_2O$; HCl) 152° C (d). (Found; C, 60.74; H, 4.94; N, 4.87; $C_{14}H_{13}NO_5$ requires C, 61.09; H, 4.76; N, 5.09%).

EXAMPLE 13 a. 6,7-Tetramethylene-1-tetralone 4-(3',4'-Tetramethylenphenyl) butanoic acid (33g; 0.14 mole) was cyclised with 85% polyphosphoric acid as described in example 8(a) to yield 24.04g (85%) of tetralone b.p.$_{0.3}$ 146°–148° C. The product solidified in the receiver and was recrystallised from light petrol [bp 40°–60°] to give m.p. 48° C. (Found; C, 84.15; H, 8.21; $C_{14}H_{16}O$ requires; C, 83.96; H, 8.05%).

b. 2-Hydroxy-6,7-tetramethylene-1,4-naphthoquinone

Autoxidation of 6,7-tetramethylenet-1-tetralone (15.0g 0.0694 mole) according to the procedure of example 8(b) gave after recrystallisation from aqueous ethano, 2,96g (17%) of material of m.p. 193° C. (Found; C, 73.44; H, 5.34; $C_{14}H_{12}O_3$ requires; C, 73.67; H, 5.30%).

c. 2-Hydroxy-3-nitro-6,7-tetramethylene-1,4-naphtoquinone

Nitration of 2-hydroxy-6,7-tetramethylene-1,4-naphthoquinone (lg) in chloroform as described in example 1(a) gave 0.97g (81%) of yellow nitro derivative of m.p. 149° C (d). Recrystallisation from aqueous ethanol; hydrochloric acid raised the m.p. to 195°–196° C (d). (Found; C, 61.52; H, 4.10; N, 4.87; $C_{14}H_{11}NO_5$ requires; C, 61.54; H, 4.06; N, 5.13%).

EXAMPLE 14 a. 7-Phenyl-1-tetralone 4- (4'-Biphenylyl) butanoic acid (80g, 0.333 mole m.p. 116° C prepared by the Clemmensen reduction of 3-(4'-biphenylycarbonyl) propanoic acid) was cyclised with 85% polyphosphoric acid as described in example 8(a) to give 20.98g (30%) of the tetralone m.p. 67° C after recrystallisation from 40–60 petrol. (Found; C, 86.30; H, 6.53; $C_{16}H_{14}O$ requires; C, 86.45; H, 6.35%).

b. 2-Hydroxy-7-phenyl-1,4-naphthoquinone

Autoxidation of 7-phenyl-1-tetralone (19g; 0.085 mole) according to the procedure of example 8(b) gave after recrystallisation from ethanol in the presence of charcoal 9.47g (44%) of yellow product of m.p. 190°–192° C. A further recrystallisation gave m.p. 192° C. (Found; C, 86.68; H, 4.03; $C_{16}H_{10}O_3$ requires; C, 76.69; H, 4.03%).

c. 2-Hydroxy-3-nitro-7-phenyl-1,4-naphthoquinone

Nitration of 2-hydroxy-7-phenyl-1,4-naphthoquinone (2.0g) as described in example 1(a) afforded 2.14g (91%) of 3-nitro derivative of m.p. 164° C (d). Recrystallisation from ethanol; hydrochloric acid gave m.p. 172°–173° C. (Found; C, 64.73; H, 3.34; N, 4,78; $C_{16}H_9NO_4$ requires; C, 65.09; H, 3.05; N, 4.79%).

All of the compounds of the formula (I) prepared in the preceding examples were tested in the rat Passive Cutaneous Anaphylaxis Test (PCA test) described below. They were administered as their sodium salts either in pH 7.2 phosphate buffer (for soluble salts) or as a suspension in 1% methyl cellulose (for insoluble salts).

i. Serum containing heat labile homocytotropic antibody was raised in rats by a method similar to that used by Mota. (I. Mota, *Immunology*, 1964, 7, 681)

Male Wistar rats of 250–300 g were injected intraperitoneally with 0.5 ml. of *Bordatella pertussis* vaccine (containing 4 × $10^{10}$ dead organism per ml) and subcutaneously with 0.5 ml. of an emulsion of 100 mg of ovalbumin in 2 ml. of saline and 3 ml. of incomplete Freunds' adjuvant. Rats were bled by cardiac puncture on day 18, the blood was pooled and separated and serum stored at −20° and thawed only once before use.

ii. The P.C.A. test was similar to that described by Ovary and Bier (A. Ovary and O. E. Bier, *Prod. Soc. Exp. Biol. Med.*, 1952, 81, 584) and Goose and Blair (J. Goose and A.M.J.N. Blair, *Immunology*, 1969, 16, 769).

0.1 ml. of each of six twofold serial dilutions of the serum in 0.9% saline were injected intradermally into separate sites on the shaved dorsal surface of 250–350 g. Male Wister rats. 72 hours later the animals were challenged by i.v. injection of 0.3 ml. of 1% ovalbumin mixed with 0.1 ml. of a 5% solution of pontamine sky blue dye both in isotonic saline buffered with pH 7.2 Sorenson buffer (P.B.S.). The rats were killed after 20 minutes and the diameter of the blue wheals at the antibody injection sites were measured. The starting dilution of the serum was adjusted so that there was no response, after challenge, at the site of injection of the highest dilution and a maximum response at the two or three lowest dilutions. Typically, six twofold serial dilutions of the serum ¼ to 1/128 were used.

Compounds were tested for their ability to reduce the diameter of the wheals at the injection sites of dilutions of antibody which on all the controls have less than maximum response. Amounts of the compounds were administered to rats by subcutaneous injection, into the nucal region, of a solution of the compound in P.B.S. or as a suspension in 1% methyl cellulose, each amount to a test group of six animals at a specified time prior to intravenous challenge with ovalbumin. The diameters of the blue wheals which developed on the test group of animals were compared to those on a control group of six animals treated in the same way as the test group, but which had received an equivalent subcutaneous injection of the carrier fluid of the same volume but not containing the compound under test.

$$\%\text{Inhibition of P.C.A.} = 100\left(1 - \frac{a}{b}\right)$$

$a =$ The mean of the sum of the diameters of the wheals produced in the test group of animals at those antibody sites where all the control group of animals gave less than maximum response.

$b =$ The mean of the sum of diameters of the wheals produced in the control group of animals at those antibody sites where all the animals in group gave less than maximum response.

The preferred method of administration was a solution of the test compound dissolved in pH 7.2 buffer and neutralized with sodium bicarbonate. For those compounds having insoluble sodium salts, the salts were isolated by reaction of the free nitro compound with 2.5N sodium hydroxide and the filtered sodium salt washed free of alkali with water. The dried salts were then administered as a suspension in 1% methyl cellulose.

| Biological Results: | Dose (mg/Kg) | Time (mins) | % Inhibition of PCA response |
|---|---|---|---|
| Example 1 | 25 | 0 | 31 |
| | 100 | 0 | 32 |
| | 25 | 30 | 16 |
| | 100 | 30 | 30 |
| Example 2 | 25 | 0 | 15 |
| | 100 | 0 | 56 |
| | 25 | 30 | 33 |
| | 100 | 30 | 30 |
| Example 3 | 25 | 0 | 24 |
| | 72 | 0 | 44 |
| | 25 | 30 | 14 |
| | 72 | 30 | 18 |
| Example 4 | 0.5 | 10 | 6 |
| | 1.0 | 10 | 16 |
| | 2.0 | 10 | 16 |
| | 4.0 | 10 | 29 |
| Example 5 | 5 | 10 | 22 |
| | 10 | 10 | 41 |
| | 20 | 10 | 65 |
| | 40 | 10 | 85 |

-continued
| Biological Results: | Dose (mg/Kg) | Time (mins) | % Inhibition of PCA response |
|---|---|---|---|
Example 6
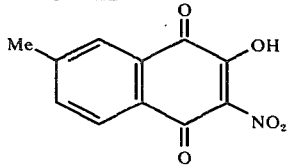
| | 5 | 10 | 19 |
| | 10 | 10 | 36 |
| | 20 | 10 | 33 |
| | 40 | 10 | 52 |
Example 7
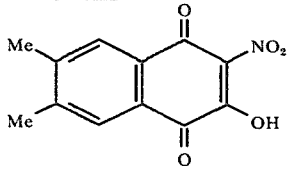
| | 25 | 0 | 62 |
| | 100 | 0 | 90 |
| | 25 | 30 | 18 |
| | 100 | 30 | 27 |
Example 8
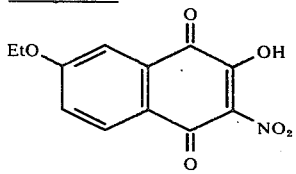
| | 5 | 10 | 25 |
| | 10 | 10 | 28 |
| | 20 | 10 | 54 |
| | 40 | 10 | 79 |
Example 9
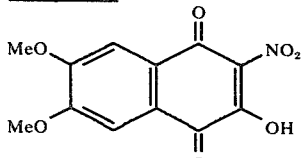
| | 5 | 10 | 28 |
| | 10 | 10 | 39 |
| | 20 | 10 | 75 |
| | 40 | 10 | 84 |
Example 10
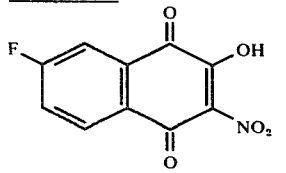
| | 100 | 10 | 5 |
| | 100 | 30 | 13 |
Example 11
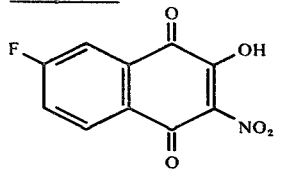
| | 100 | 10 | 13 |
| | 100 | 30 | 16 |
Example 12
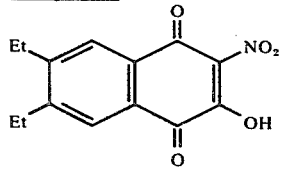
| | 1 | 10 | 11 |
| | 2 | 10 | 23 |
| | 4 | 10 | 26 |
| | 8 | 10 | 55 |
Example 13
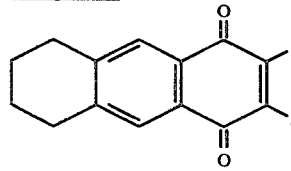
| | 5 | 10 | 72 |
| | 10 | 10 | 80 |
| | 20 | 10 | 87 |
| | 40 | 10 | 90 |
Example 14

| Biological Results: | Dose (mg/Kg) | Time (mins) | % Inhibition of PCA response |
|---|---|---|---|
| 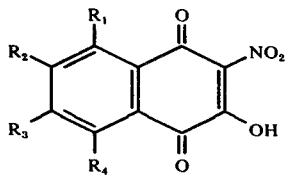 | 10 | 10 | 20 |
| | 20 | 10 | 12 |
| | 40 | 10 | 23 |
| | 80 | 10 | 23 |

We claim:

1. A pharmaceutical composition in a form suitable for oral, parenteral or insufflation administration to humans which comprises an amount of

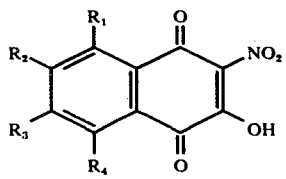

or a pharmaceutically acceptable, nontoxic salt thereof, wherein $R_1$, $R_2$, $R_3$ and $R_4$ are each hydrogen, lower alkyl, lower alkoxy, phenyl, hydroxy or halogen, or any adjacent two of $R_1$, $R_2$, $R_3$ and $R_4$ taken together with the carbon atoms to which they are joined form a 5- or 6-membered carbocyclic ring, provided that $R_1$, $R_2$, $R_3$ and $R_4$ are not all hydrogen, sufficient to be effective for the prophylaxis of asthma, hayfever or rhinitis, in combination with a pharmaceutically acceptable nontoxic carrier suitable for said administration form.

2. A pharmaceutical composition according to claim 1 wherein $R_1$ and $R_4$ are each hydrogen, $R_2$ and $R_3$ are each hydrogen, or lower alkyl or $R_2$ and $R_3$ taken together with the carbon atoms to which they are joined form a cyclohexenyl or cyclopentenyl ring, provided that $R_1$, $R_2$, $R_3$ and $R_4$ are not all hydrogen.

3. A composition according to claim 1 wherein $R_1$, $R_2$, $R_3$ and $R_4$ are each hydrogen, fluorine, chlorine, bromine, iodine, alkyl of 1 to 3 carbon atoms, alkoxy of 1 to 4 carbon atoms or phenyl, or $R_1$ and $R_2$, $R_2$ and $R_3$ or $R_3$ and $R_4$, taken together with the carbon atoms to which they are joined form a benzene, cyclohexenyl or cyclopentenyl ring.

4. A pharmaceutical composition according to claim 1 wherein $R_1$ and $R_4$ are each hydrogen, $R_2$ and $R_3$ are each methyl, ethyl, n-propyl, methoxy, ethoxy, or n-propoxy or $R_2$ and $R_3$, together with the carbon atoms to which they are joined, form a cyclohexenyl or cyclopentenyl ring.

5. A pharmaceutical composition according to claim 1 wherein the compound is in the form of an alkali metal salt, an alkaline earth metal salt, an amine salt or amino salt.

6. A pharmaceutical composition according to claim 1 wherein the compound is present in the form of a salt.

7. A pharmaceutical composition according to claim 6 wherein the salt is the sodium salt.

8. A pharmaceutical composition according to claim 1 which is in the form of a microfine powder for insufflation.

9. A pharmaceutical composition according to claim 8 which additionally contains a bronchodilator.

10. A pharmaceutical composition according to claim 9 wherein the bronchodilator is isoprenaline.

11. A pharmaceutical composition according to claim 1 wherein the carrier is a sterile liquid carrier suitable for injection.

12. A pharmaceutical composition claim 1 wherein the carrier is a solid carrier.

13. The pharmaceutical composition according to claim 1 wherein the compound is in the form of the sodium, potassium, magnesium or aluminum salt.

14. A pharmaceutical composition according to claim 2 wherein the compound is 2-hydroxy-6,7-dimethyl-3-nitro-1,4-naphthoquinone.

15. A pharmaceutical composition according to claim 2 wherein the compound is 2-hydroxy-6,7-diethyl-3-nitro-1,4-naphthoquinone.

16. A pharmaceutical composition according to claim 2 wherein the compound is 2-hydroxy-6,7-trimethylene-3-nitro-1,4-naphthoquinone.

17. A pharmaceutical composition according to claim 2 wherein the compound is 2-hydroxy-6,7-tetramethylene-3-nitro-1,4-naphthoquinone.

18. A method for the prophylaxis of asthma, hayfever and rhinitis in humans which comprises administering to a human in need thereof orally, parenterally or by insufflation an amount of a compound of the formula or a pharmaceutically acceptable, nontoxic salt thereof, wherein $R_1$, $R_2$, $R_3$ and $R_4$ are each hydrogen, lower alkyl, lower alkoxy, phenyl, hydroxy or halogen, or any adjacent two of $R_1$, $R_2$, $R_3$ and $R_4$ taken together with the carbon atoms to which they are joined form a 5- or 6-membered carbocyclic ring, provided that $R_1$, $R_2$, $R_3$ and $R_4$ are not all hydrogen, sufficient to be effective for the prophylaxis of asthma, hayfever or rhinitis in combination with a pharmaceutically acceptable nontoxic carrier suitable for said administration form.

19. A method according to claim 18 wherein $R_1$ and $R_4$ are each hydrogen, $R_2$ and $R_3$ are each hydrogen, or lower alkyl, or $R_2$ and $R_3$ taken together with the carbon atoms to which they are joined form a cyclohexenyl or cyclopentenyl ring, provided that $R_1$, $R_2$, $R_3$ and $R_4$ are not all hydrogen.

20. A method according to claim 18 wherein $R_1$, $R_2$, $R_3$ and $R_4$ are each hydrogen, fluorine, chlorine, bromine, iodine, aklyl of 1 to 3 carbon atoms, alkoxy of 1 to 4 carbon atoms or phenyl, or $R_1$ and $R_2$, $R_2$ and $R_3$ or $R_3$ and $R_4$, taken together with the carbon atoms to which they are joined form a benzene, cyclohexenyl or cyclopentenyl ring.

21. A method according to claim 18 wherein $R_1$ and $R_4$ are each hydrogen, $R_2$ and $R_3$ are each methyl, ethyl, n-propyl, methoxy, ethoxy, or n-propoxy, or $R_2$ and $R_3$ together with the carbon atoms to which they are joined, form a cyclohexenyl or cyclopentenyl ring.

22. A method according to claim 18 wherein the compound is present in the form of a salt.

23. A method according to claim 18 wherein the compound is in the form of an alkali metal salt, an alkaline earth metal salt, an amine salt or amino salt.

24. The method according to claim 18 wherein the compound is in the form of the sodium, potassium, magnesium or aluminum salt.

25. A method according to claim 22 wherein the salt is the sodium salt.

26. A method according to claim 18 wherein the composition is in the form of a microfine powder for insufflation.

27. A method according to claim 26 which additionally contains a bronchodilator.

28. A method according to claim 27 wherein the bronchodilator is isoprenaline.

29. A method according to claim 18 wherein the carrier is a sterile liquid carrier suitable for injection.

30. A method according to claim 18 wherein the carrier is a solid carrier.

31. A method according to claim 19 wherein the compound is 2-hydroxy-6,7-dimethyl-3-nitro-1,4-naphthoquinone.

32. A method according to claim 19 wherein the compound is 2-hydroxy-6,7-diethyl-3-nitro-1,4-naphthoquinone.

33. A method according to claim 19 wherein the compound is 2-hydroxy-6,7-trimethylene-3-nitro-1,4-naphthoquinone.

34. A method according to claim 19 wherein the compound is 2-hydroxy-6,7-tetramethylene-3-nitro-1,4-naphthoquinone.

* * * * *